US008935196B2

(12) United States Patent
Zillner

(10) Patent No.: US 8,935,196 B2
(45) Date of Patent: Jan. 13, 2015

(54) SYSTEM AND METHOD FOR PROVIDING INSTANCE INFORMATION DATA OF AN INSTANCE

(75) Inventor: Sonja Zillner, München (DE)

(73) Assignee: Siemens Aktiengesellschaft, Munich (DE)

( * ) Notice: Subject to any disclaimer, the term of this patent is extended or adjusted under 35 U.S.C. 154(b) by 326 days.

(21) Appl. No.: 12/846,932

(22) Filed: Jul. 30, 2010

(65) Prior Publication Data

US 2011/0295790 A1    Dec. 1, 2011

(30) Foreign Application Priority Data

May 28, 2010   (EP) ..................................... 10005595

(51) Int. Cl.
*G06N 5/02*       (2006.01)
*G06F 19/00*      (2011.01)
(52) U.S. Cl.
CPC ................ *G06N 5/02* (2013.01); *G06F 19/321* (2013.01)
USPC .......................................................... 706/55
(58) Field of Classification Search
CPC ................................ G06N 5/02; G06F 19/321
USPC ....................................................... 706/55, 12
See application file for complete search history.

(56) References Cited

U.S. PATENT DOCUMENTS

| | | | |
|---|---|---|---|
| 7,027,974 B1 * | 4/2006 | Busch et al. ........................ 704/4 |
| 7,493,333 B2 * | 2/2009 | Hill et al. .............................. 1/1 |
| 7,496,593 B2 * | 2/2009 | Gardner et al. ......................... 1/1 |
| 2005/0209519 A1 * | 9/2005 | Krishnan et al. ............... 600/437 |
| 2006/0047632 A1 * | 3/2006 | Zhang .................................. 707/3 |
| 2006/0053098 A1 * | 3/2006 | Gardner et al. ..................... 707/3 |
| 2008/0027917 A1 * | 1/2008 | Mukherjee et al. ................ 707/3 |
| 2008/0201280 A1 * | 8/2008 | Martin et al. .................... 706/12 |
| 2009/0313243 A1 * | 12/2009 | Buitelaar et al. .................. 707/5 |

OTHER PUBLICATIONS

Moller M. et al., "RadSem: Semantic Annotation and Retrieval for Medical Images", Proceedings of the 6th European Semantic Web Conference, ESWC, Herakalion, Crete, Greece, pp. 21-35, May 2009.*
Zillner S. et al., "Semantic Visualization of Patient Information", 21st IEEE Symposium on Computer-Based Medical Systems, CBMS, pp. 296-301, 2008.*
Zhou X. et al., "Semantics and CBIR: A Medical Imaging Perspective", CIVR, Niagara Falls, Ontario, Canada, Jul. 7-9, pp. 571-580, 2008.*

(Continued)

*Primary Examiner* — Alan Chen
*Assistant Examiner* — Dave Misir
(74) *Attorney, Agent, or Firm* — King & Spalding L.L.P.

(57) ABSTRACT

A method and system for providing instance information data of at least one instance. The method has the steps of generating a semantic representation of the instance on the basis of at least one instance data source, providing a semantic representation of a domain on the basis of at least one structured domain data source, performing an integration of the semantic instance and domain representations to provide an integrated semantic representation and deriving automatically instance information data from the provided integrated semantic representation. The method and system allow to provide efficiently instance information data of a wide range of instances with technical entities and persons, in a particular patients in different domains such as radiology or anatomy.

15 Claims, 2 Drawing Sheets

(56) References Cited

OTHER PUBLICATIONS

Moller M. et al., "A Generic Framework for Semantic Medical Image Retrieval", Proceedings of the Knowledge Acquisition from Multimedia, 2007.*

Moller M. et al., "Medical Image Understanding Through the Integration of Cross-Modal Object Recognition With Formal Domain Knowledge", Proceeding of HEALTHINF, vol. 1, Funchal, Madeira, Portugal, pp. 134-141, 2008.*

Wennerberg P. et al., "Towards a Human Anatomy Data Set for Query Pattern Mining based on Wikipedia and Domain Semantic Resources", ELDA, pp. 59-65, 2008.*

Rubin D. et al., "Annotation and Image Markup: Accessing and Interoperating with the Semantic Content in Medical Imaging", IEEE Intelligent Systems, pp. 57-65, Jan./Feb. 2009.*

Rubin D. et al., "Medical Imaging on the Semantic Web: Annotation and Image Markup", AAAI, 2008.*

Rubin D., "Creating and Curating a Terminology for Radiology: Ontology Modeling and Analysis", Journal of Digital Imaging, vol. 21, No. 4, pp. 355-362, Dec. 2008.*

Wennerberg P. et al., "Deriving Clinical Query Patterns from Medical Corpora Using Domain Ontologies", Workshop on Biomedical Information Extraction, Borovets, Bulgaria, pp. 50-56, Sep. 2009.*

Zillner S., "Towards the Ontology-based Classification of Lymphoma Patients using Semantic Image Annotations", Proceedings of SWAT4LS, Amsterdam, 2009.*

Sonntag D. et al., "Applications of an Ontology Engineering Methodology Accessing Linked data for Dialogue-Based Medical image Retrieval", AAAI, pp. 120-125, 2010.*

Gruninger, Michael et al., "The Design and Evaluation of Ontologies for Enterprise Engineering," Department of Industrial Engineering, University of Toronto, 14 pages, 1994.

Bouaud, J. et al., "Methodological Principles for Structuring 'Ontology'," DIAM Rapport Interne RI-95-148, IJCAI Workshop on Basic Ontological Issues in Knowledge Sharing, 7 pages, Aug. 19, 1995.

Uschold, Mike et al., "Ontologies: Principles, Methods and Applications," Knowledge Engineering Review, vol. 11, No. 2, 69 pages, Feb. 1996.

Uschold, Mike, "Building Ontologies: Towards a Unified Methodology," Proceedings of Expert Systems, the 16th Annual Conference of the British Computer Society Specialist Group on Expert Systems, 20 pages, Sep. 1996.

Jones, Dean et al., "Methodologies for Ontology Development," Department of Computer Science, University of Liverpool, 14 pages, 1998.

Schreiber, G. et al., "Knowledge Engineering and Management," The CommonKADS Methodology, The MIT Press, Book abstract, 1 page, 1999.

López, Mariano Fernández et al., "Building a Chemical Ontology Using Methontology and the Ontology Design Environment," IEEE Intelligent Systems, 10 pages, Jan. 1999.

Sure, York et al., "On-To-Knowledge Methodology—Final Version," EU-IST Project IST-1999-10132, 81 pages, 2002.

Baader, Franz et al. (Eds), "The Description Logic Handbook: Theory, Implementation, and Applications," Cambridge University Press, 500 pages, 2003.

Dameron, Olivier et al., "Grading Lung Tumors Using OWL-DL Based Reasoning," Proceedings of 9th International Protégé Conference, 4 pages, 2003.

Hu, Bo et al., "Ontology-Based Medical Image Annotation with Description Logics," Proceedings of the 15th IEEE International Conference on Tools with Artificial Intelligence, 6 pages, 2003.

Brachmann, R. et al., "Knowledge Representation and Reasoning," 179 pages, Jul. 17, 2003.

Rosse, Cornelius et al., "A Reference Ontology for Biomedical Informatics: the Foundational Model of Anatomy," Journal of Biomedical Informatics, vol. 36, 23 pages, Nov. 7, 2003.

Golbreich, Christine et al., "What Reasoning Support for Ontology and Rules? The Brain Anatomy Case Study," Proceedings of the Workshop on OWL Experiences and Directions, 12 pages, 2005.

Wittekind, Christian et al., "TNM: Klassifikation Maligner Tumoren," Book Abstract, 4 pages, 2005.

Marquet, Gwenaëlle et al., "Grading Glioma Tumors Using OWL-DL and NCI Thesaurus," Proceedings of the American Medical Informatics Association Conference (AMIA), 5 pages, 2007.

Seifert, S. et al., "Hierarchical Parsing and Semantic Navigation of Full Body CT Data," SPIE Medical Imaging, 4 pages, 2009.

Horridge, Matthew et al., "The OWL API: A Java API for Working with OWL 2 Ontologies," Proceedings of OWL: Experiences and Directions, 10 pages, 2009.

Channin, David et al., "The caBIG™ Annotation and Image Markup Project," Journal of Digital Imaging, 9 pages, Mar. 18, 2009.

Zillner, Sonja, "Patient Classification Using Semantic Image Annotations," Corporate Technology, Siemens AG, Munich, Germany, 15 pages, 2010.

* cited by examiner

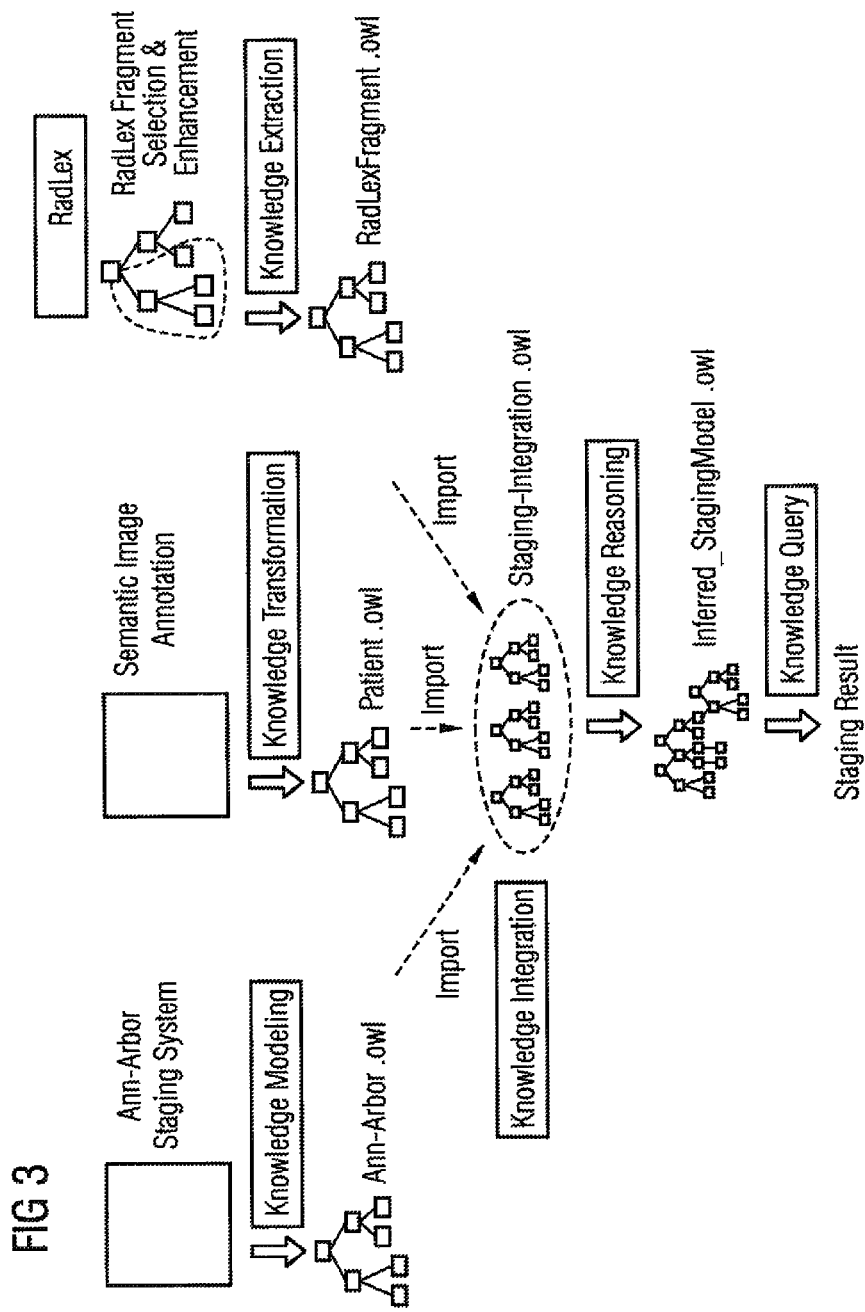

SYSTEM AND METHOD FOR PROVIDING INSTANCE INFORMATION DATA OF AN INSTANCE

CROSS-REFERENCE TO RELATED APPLICATIONS

This application claims priority to EP Patent Application No. 10005595 filed May 28, 2010. The contents of which is incorporated herein by reference in its entirety.

TECHNICAL FIELD

The invention provides a system and a method for providing instance information data of at least one instance such as a patient and in particular a system for providing a reasoning framework for integrating heterogeneous data resources.

BACKGROUND

In general instances are formed by objects such as persons or components. These persons can be for example patients having one or several diseases to be diagnosed and treated by a person working in a hospital. An object can also be technical components such as machine component of a technical system consisting of one or plurality of objects or technical entities.

Clinicians rely heavily on images for screening, diagnosis and treatment planning. Despite the wide range of different imaging technologies and their respective advanced techniques for analysis, gaps still remain as far as methods for a generic image understanding are concerned. There exist several approaches for semantic image annotation such as automatic image passing, manual image annotation or automatic extraction of information from data sources such as annotated images or radiology reports. Although the existing approaches provide a basis for the processing of semantic representations of an instance such as a patient, they do not yet make use of practical clinical knowledge such as best practise solutions or clinical guidelines to customize the established annotations to reflect particular requirements of the respective application or workflow.

SUMMARY

According to various embodiments, a method and a system can be provided which provide a reasoning framework for integration of heterogeneous instance and domain data sources.

According to an embodiment, a method for providing instance information data of at least one instance may comprise: generating a semantic representation of said instance on the basis of at least one instance data source; providing a semantic representation of a domain on the basis of at least one structured domain data source; performing an integration of the semantic instance and domain representations to provide an integrated semantic representation; and deriving automatically instance information data from the provided integrated semantic representation.

In a possible embodiment of the method, the semantic representation of said instance comprises an instance ontology.

In a possible embodiment of the method, the semantic representation of said domain comprises a domain ontology.

In a possible embodiment of the method, the instance is an object formed by a person or by a component.

In a possible embodiment of the method, the instance ontology and the domain ontology are stored as web ontology language (OWL) files.

In a possible embodiment of the method, the semantic representation of said instance is generated by transforming annotated images taken of said instance by means of at least one image detection device into said semantic representation of said instance.

In a possible embodiment of the method, upon transforming annotated images of said instance into said semantic representation of said instance attributes of said instance are classified automatically on the basis low-level data information, such as image coordinates.

In a possible embodiment of the method, the semantic representation of said domain is provided by extracting said semantic representation of said domain from a semantic representation of a top-level domain.

In a possible embodiment, the semantic representation of said top-level domain is formed by a semantic representation of the anatomy domain or the radiology domain.

In a possible embodiment of the method, the integrated semantic representation is adapted to perform a semantic annotation of said instance.

In an alternative embodiment of the method, the integrated semantic representation is adapted to perform a decision support for classification of said instance.

In a further embodiment of the method, the integrated semantic representation is adapted to perform an instance search.

In a further possible embodiment of the method, the integrated semantic representation is adapted to perform an instance process control.

According to yet another embodiment, a system for providing instance information data of at least one instance may comprise: at least one database storing a semantic representation of said instance and a semantic representation of a domain; and a processing unit for performing an integration of the semantic instance and domain representations to provide an integrated semantic representation stored in a memory and deriving automatically instance information data from the stored integrated semantic representation.

In a possible embodiment of the system, said semantic representation of said instance is an instance ontology stored in a first database.

In a possible embodiment of the system, said semantic representation of said domain is a domain ontology stored in a second database.

In a possible embodiment of the system, said instance ontology is stored as a web ontology language (OWL) file in said first database.

In a possible embodiment of the system, the domain ontology is stored as a web ontology language (OWL) file in said second database.

In a possible embodiment of the system, said processing unit is adapted to execute a reasoning engine which derives automatically the instance information data from the integrated semantic representation stored in said memory.

In a possible embodiment of the system, said semantic representation of said instance is generated by a transformation unit which transforms annotated images of said instance into said semantic representation of said instance.

In a possible embodiment of the system, said annotated images are provided by an annotation unit for annotating instance images taken of the instance.

In a possible embodiment, the instance images are generated by means of image detection devices.

In a possible embodiment of the system, the image detection devices comprise a computer tomograph, a magnet resonance imaging device, an ultrasound detection device and a positron emission tomograph.

In a possible embodiment of the system, said semantic representation of a domain comprises an Ann-Arbor Staging document providing a classification of lymphoma patients in terms of disease progression, a foundation model of anatomy (FMA) ontology and a radiology lexicon (RadLex) ontology.

BRIEF DESCRIPTION OF THE DRAWINGS

FIG. 3 shows a diagram of an exemplary embodiment of a system for providing instance information data of a patient.

DETAILED DESCRIPTION

In the following possible embodiments of a system and a method for providing instance information data of at least one instance are described with reference to the enclosed figures.

Figure 1:
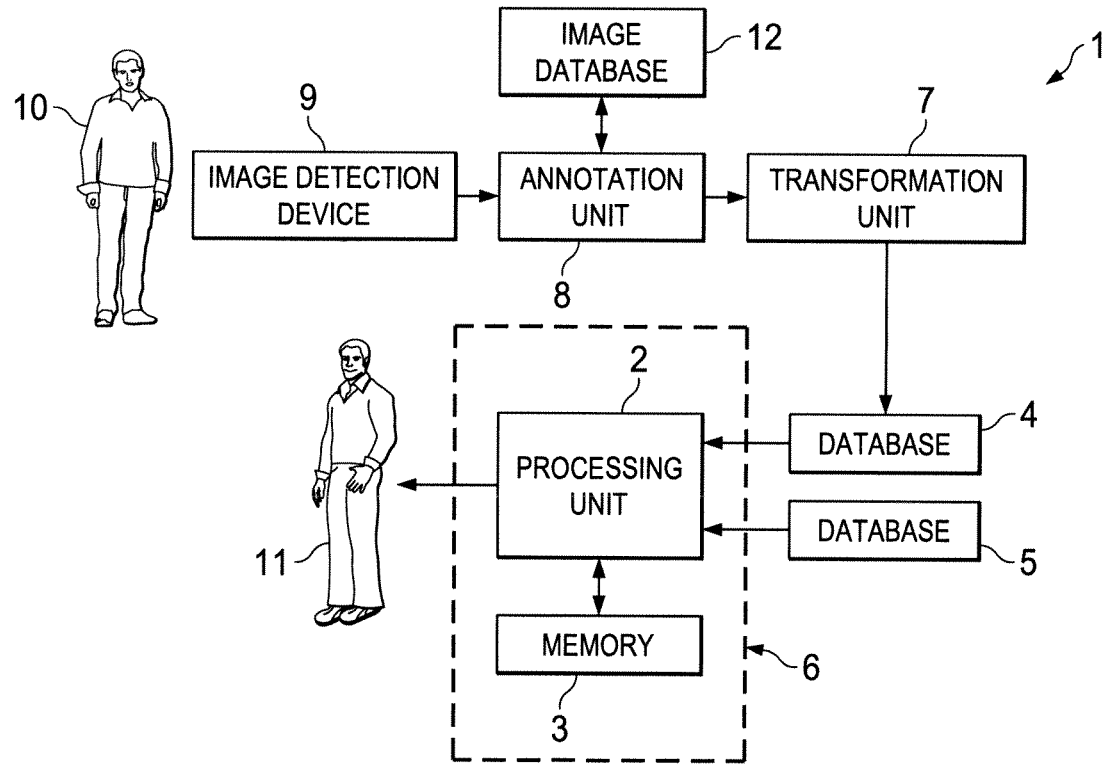
FIG. 1 shows a block diagram of a possible embodiment of a system for providing instance information data.

As can be seen from FIG. 1 a system 1 for providing instance information data of at least one instance according to the shown embodiment comprises a processing unit 2 for performing an integration of a semantic instance representation and at least one domain representation to provide an integrated semantic representation which can be stored in a memory 3. The processing unit 2 derives automatically instance information data from the stored integrated semantic representation. In a possible embodiment the semantic representation of the instance is an instance ontology and the semantic representation of the domain is a domain ontology as illustrated in FIG. 1.

The processing units 2 can be formed by a data processing unit comprising at least one microprocessor executing a reasoning engine for a reasoning application program to derive automatically the instance information data of the respective instance.

An instance can be formed for example by a person, in particular by a patient to be treated. In a possible embodiment the reasoning engine or reasoning application program can be loaded from a configuration memory or program memory. In a possible embodiment the reasoning engine can be selected by a user such as a physician in a hospital depending on the respective use case, for example to perform a semantic annotation of the respective instance or to provide a medical decision support for classification of the instance. Furthermore, the physician may select a reasoning engine for performing an instance search in a data base or to perform an instance process control.

In possible embodiments the processing unit 2 is connected to a user interface to select the reasoning engine for the specific purpose or use case. In a possible embodiment the processing unit 2 as shown in FIG. 1 comprises a first interface for receiving an instance ontology of the respective instance and a second interface for receiving the at least one domain ontology of the respective domain. In a possible embodiment the instance ontology is loaded from a first database 4 and the domain ontology is loaded from a second database 5. The databases 4, 5 can be local databases or remote databases connected to the processing unit 2 via a network such as the Internet.

The processing unit 2 shown in FIG. 1 as well as the memory 3 adapted to store the integrated semantic representation can be provided in a terminal device 6 which can have additional units such as a user interface or a program memory storing one or several executable reasoning engines. The terminal device 6 can be also a mobile device carried by a user such as a doctor working in a hospital. In a possible embodiment the instance ontology is stored as a web ontology language (OWL) file in the first data base 4. At least one domain ontology can be stored as one or several web ontology language (OWL) files in the second database 5. The processing unit 2 is adapted to execute a reasoning engine which derives automatically the instance information data required by a user from the integrated semantic representation stored in the memory 3. The processing unit 2 performs an integration of the semantic instance representation, i.e. the instance ontology or instance ontology OWL file, and the semantic domain representations, i.e. the domain ontologies or domain OWL files stored in the second database 5.

In the embodiments shown in FIG. 1 the semantic representation of the instance (e.g. patient) is generated by a transformation unit 7 which transforms annotated images of said patient into the semantic representation of the patient, i.e. the instance ontology stored in the first database 4. The annotated images are provided by an annotation unit 8 for annotating instance images taken of the respective instance, e.g. a patient. The annotation unit 8 receives images from at least one image detection device 9. This image detection device 9 can be formed by a computer tomograph. In a further possible embodiment the image detection device 9 is a magnet resonance imaging device MRI. In another embodiment the image detection device 9 is an ultrasound detection device. In a further embodiment the image detection device 9 is a positron emission tomograph PET. The image detection device 9 generates images of an instance 10 such as a patient. The instance 10 can be any kind of object such as a person or a component. The person can be a patient to be treated having one or several diseases. The instance 10 can also be a physical object or entity such as a machine component. Further the instance 10 can be a complex component such as a car or an industrial manufacturing system. The detection devices 9 can be connected by data transmission lines or a network to the annotation unit 8. A user 11, for example a physician working in a hospital, can perform an annotation of the generated images to generate annotated images by means of the annotation unit 8. In a possible embodiment the annotated images are stored in an image database 12 connected to the annotation unit 8. Annotated images are supplied by the annotation unit 8 to a transformation unit 7 which translates the structured patient data comprising annotated images into patient OWL files to be stored in the first database 4. The transformation can be performed in an automatic manner. In a possible embodiment the transformation is performed by executing a program such as an OWL API.

In a possible embodiment the domain ontology stored in the second database 5 is extracted from a semantic representation of a domain, in particular a top level domain including an anatomy domain and a radiology domain. These kind of top level domains form external knowledge resources which can be selected in a possible embodiment by the user 11 by means of a user interface of the terminal 6. An extraction of a specific domain ontology from a top level domain ontology can be formed by a zooming process to cut out fragments of an existing top level domain ontology stored in a public database accessible via a data network. In a possible embodiment more than one domain ontologies can be used to provide the integrated semantic representation stored in the memory 3.

In a possible embodiment the annotation unit 8 and the transformation unit 7 are integrated in the terminal 6. The terminal 6 can also have an integrated image detection device 9 which can be a digital camera to take pictures of an instance or object 10.

A semantic image annotation can be performed by means of the annotation unit 8 by a person or user 11 viewing the image explicitly or by means of a formal description. The labelling of semantic images can be performed in a possible embodiment automatically. In alternative embodiments the labelling can be performed semi-automatically or manually. Several approaches for semantic image annotation can be used such as automatic image parsing, manual image annotation as well as the extraction of information from DICOM headers and DICOM structured reports, or the automated extraction from radiology reports. It is further possible that a user 11 manually adds semantic image annotations by selecting or defining anatomical landmarks or arbitrary regions or respectively volumes of interest. The system 1 according to various embodiments can make use of explicit clinical experience knowledge such as best practise solutions for clinical guidelines for fine tuning and customizing established annotations to reflect particular requirements of a clinical application or workflow. The system 1 can use heterogeneous knowledge resources ranging from text documents, annotated images to structured domain ontologies or taxonomies. The system 1 according to various embodiments is not restricted to a use case in the medical domain but can also be operated in other domains such as technical systems or apparatuses.

Figure 2:
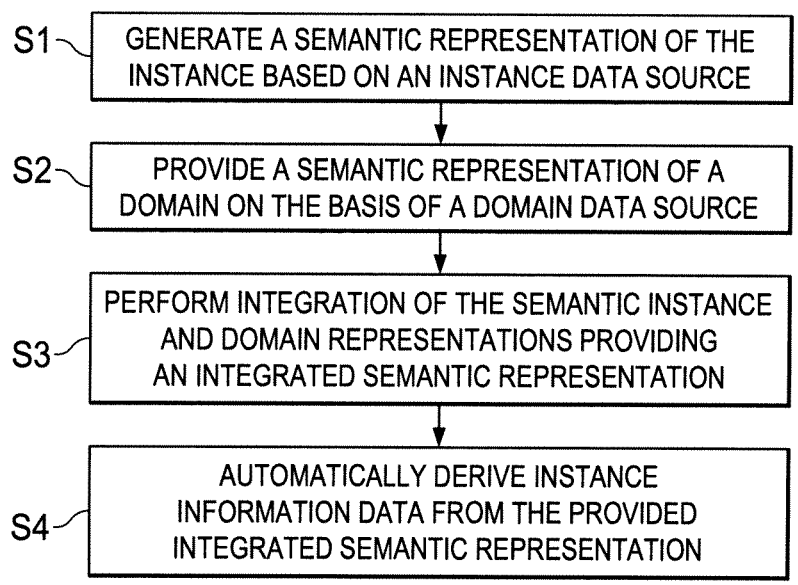
FIG. 2 shows a flowchart of a possible embodiment of a method for providing instance information data.

FIG. 2 shows a flowchart of a possible embodiment of a method for providing instance information data of at least one instance. This instance can be a patient to be treated or a technical component of a technical system.

In a first step S1 a semantic representation of the respective instance is generated on the basis of at least one instance data source. The instance data source can be for example image records of a patient.

In a further step S2 a semantic representation of a domain on the basis of at least one structured domain data source is provided. This semantic representation can comprise a domain ontology. This domain ontology can be formed by a part or a fragment of a top level domain ontology selected by a user by means of a zooming function. In a possible embodiment the top level domain ontology is a foundation model of anatomy FMA ontology and/or a radiology lexicon (RadLex) ontology. A further possible semantic representation of a domain can comprise a text document for example an Ann-Arbor-Staging document providing a classification of patients in terms of a disease progression.

In a further step S3 the integration of the semantic instance and domain representations is performed to provide an integrated semantic representation which can be stored in the memory 3. The integration is performed by the processing unit 2. In a possible embodiment pre-processed knowledge sources are integrated as a basis for a subsequent reasoning step. This can for example be accomplished by an import functionality of the OWL representation language by a corresponding tool.

In a further step S4 instance information data is derived automatically from the provided integrated semantic representation. This step can also be performed by the processing unit 2. In a possible embodiment the processing unit 2 is adapted to execute a reasoning engine which derives automatically the instance information data from the integrated semantic representation stored in the memory 3. The derived or inferred instant information data is made accessible to a user 11. For example the user 11 can query the provided integrated semantic representation stored in the memory 3 by means of a querying mechanism such as SPARQ1. In a possible embodiment the derived instance information data of e.g. a patient can be used as a medical decision support for classification of the respective patient. It is possible to use the derived instance information data of the respective patient for an instance search or patient search to find a particular patient. Further, the derived instance information data can be used for an instance process control.

FIG. 3 shows a diagram for illustrating an exemplary embodiment of a system 1 and method for providing instance information data of at least one instance. In the shown diagram the instance is formed by a patient wherein different heterogeneous knowledge resources are used to derive automatically patient information data of the respective patient.

The reasoning-based patient classification can rely on an Ann-Arbor Staging System that operates on the number, the types and the relative position of indicated lymphatic occurrences. Each staging class is described as a defined OWL class that specifies all necessary and sufficient conditions. Due to its complexity, one can break down the staging requests into simpler questions which are required to take into account the future ontology design. This simpler question can be represented as defined OWL classes, enabling the patient to be classified in accordance with predetermined criteria, that is, e.g. according to the number, type and relative position of lymphatic occurrences. The ontological model that captures the rational of the Ann-Arbor Staging System can be modelled manually. To enable the classification in accordance to the staging system, the design of the ontological model needs to reflect the processing steps and inference rules of the reasoning engine. Thus, the knowledge model also determines the ontological structure of other knowledge resources, i.e. the OWL representation of patient information and RadLex Fragment.

To achieve re-usability and interoperability of data, external medical knowledge resources as reference systems for annotation clinical data is required.

Within the MEDICO project the patient's text and image annotation relies on RadLex. To improve the scalability of the reasoning application, only the relevant information and concepts provided by the RadLex Taxonomy are integrated. For this particular use case, only the concepts describing lymphatic occurrences are of relevance. In a possible embodiment the required concepts are selected by means of text mining methods. As the intended reasoning application requires additional information—such as the position of lymphatic occurrence in relation to the diaphragm or the different types of lymphatic occurrences—the textual list of structured RadLex terms is enhanced accordingly. Subsequently, the extended list of RadLex terms can be used as input for automatically generating the RadLex fragment by using an OWL API. To be able to infer the number of different types of lymphatic occurrences, the RadLex parent-child relationship can be represented as an OWL axiom. This method can also be used to indicate the type of lymphatic occurrence—lymph node or extra nodal. Similarly, the information about the relative position of the lymphatic occurrence is incorporated by adding an OWL axiom. Due to its limited number of concepts, the RadLex Fragment paves the way for a scalable reasoning process.

The use of an Image Annotation Tool enables medical experts to provide semantic image annotation. In a possible embodiment the semantic image annotation of the patient's lymphatic occurrences is used as input for generating patient data representation in OWL. This means serializing patient's image annotation data to OWL representation language in accordance with the OWL representation of the Ann-Arbor Staging System. Patient data can be represented in two different ways, namely as a concept or as an instance. One can implement both versions and conduct scalability tests in terms of reasoning performance. To find out whether an individual belongs to a concept, one needs to propagate the information implied by what is known about all other individuals, thus, reasoning time increases polynomial to the size of the knowledge model. By representing patient information as concepts, one can achieve significant improvements in terms of reasoning performance.

To accomplish reasoning tasks, all the ontological axioms need to be imported into the knowledge model. An OWL file can be established for providing a knowledge integration 'container' to import the knowledge resources as a basis for the subsequent knowledge reasoning task. The knowledge captured in the inferred model, in particular the deducted staging information, can be queried by means of SPARQL.

One goal is to integrate practical clinical knowledge into medical applications—such as decision support systems, semantic searches or quality control applications—with a formal and explicit representation of practical clinical knowledge, paving the way towards of discovery of new classification results by means of existing reasoning procedures.

As formal representation language, it is possible to use the web ontology language (OWL). In a possible embodiment the sub-language OWL DL that is based on Description Logics is used. Description Logics, a family of formal representation languages for ontologies, are designed for classification-based reasoning.

In an embodiment three different kinds of knowledge resources were used for implementing the staging application, i.e. Ann-Arbor Staging System, an semantic image annotation an a RadLex ontology.

The Ann-Arbor Staging System establishes an explicit classification of lymphoma patients in terms of disease progression. It was initially developed for Hodgkin's Lymphoma, but is also of use for Non-Hodgkin lymphomas. The staging system depends on two criteria. The first criterion is the location of the malignant tissue, which can be identified by located biopsy as well as medical imaging methods, such as CT scanning and Positron Emission Tomography. The second criterion is systemic symptoms, such as night sweats, weight loss of more than 10 percent, or fevers caused by the lymphoma. These semantic systems are called 'B symptoms'.

The principal stage is determined by the location of the tumor and reflects the grade of expansion of lymphoma occurrences. Within this principle stage, four different stages are recognized:

Stage I indicates that the cancer is located in a single region, either an affected lymph node or organ within the lymphatic system.

In stage II the cancer is located in two separated regions, an affected lymph node or an affected organ within the lymphatic system and a second affected lymph node area. In these cases, the affected areas are confined to one side of the diaphragm—that is, both are either above or below the diaphragm.

Stage III indicates that the cancer has spread to both sides of the diaphragm, including one extra lymphatic organ or site.

Stage IV shows diffuse or disseminated involvement of one or more extra lymphatic organs.

To achieve re-usability and interoperability, it is preferred to use a third party taxonomy or ontology, as well as anatomical information to inform the application of ontological concepts describing possible regions of lymphatic occurrences, i.e. lymph node regions as well as extra lymphatic organs and sites.

Two ontologies, the Foundational Model of Anatomy (FMA) and the Radiology Lexicon (RadLex), cover anatomical entities and provide the required coverage of anatomical concepts for the staging scenario.

The FMA is a comprehensive specification of anatomy taxonomy, that is, an inheritance hierarchy of anatomical entities with different kinds of relationships. It covers approximately 70.000 distinct anatomical concepts and more than 1.5 million relations instances of 170 relation types. It provides concepts that describe single lymph nodes, such as 'auxiliary_lymph_node', as well as concepts that describe multiple lymph nodes, such as 'set_of_auxiliary_lymph_node'. It also contains 425 concepts representing singular lymph nodes and 404 concepts describing sets of lymph nodes.

RadLex is a terminology developed an maintained by the Radiological Society of North America (RSNA) for the purpose of achieving a uniform mode of indexing and the retrieval of radiology information, including medical images. RadLex contains over 8,000 anatomical and pathological terms, including imaging techniques, difficulties and diagnostic image qualities. Its purpose is to provide a standardized terminology for radiological practice. RadLex is variable in English and German and covers more than 100 concepts describing lymph node concepts.

To describe extra nodal lymphatic occurrences, any arbitrary position in the human body—except the dedicated lymph node region—can be used. As a representation of the complete complementary set of body regions proved itself to be unscalable, one can follow a pragmatic recommendation of clinical experts and limit the list of extra nodal lymphatic occurrences to a restricted number of nine body regions which are most likely to be involved.

The use case scenario relies on high-level concepts, both ontologies—FMA and RadLex—are suitable in terms of coverage. In a possible embodiment RadLex is used as a primary third party resource for annotating lymphatic occurrences in medical images. Since in a possible embodiment German radiology reports are used the German RadLex version proves to be useful. Due to the large size of Radlex, one can establish an ontology fragment, scalable and efficient enough for reasoning application. As the RadLex does not cover information about the regional relationship between concepts, the RadLex fragment is extended accordingly in a possible embodiment.

Methods for automated image parsing, enable the hierarchical—in terms of starting with the head and subsequently moving down the body—parsing of whole body CT images and the efficient segmentation of multiple organs whilst taking contextual information into account. Whilst automated image parsing remains incomplete, manual image annotation is an important complement as a user can manually add semantic image annotation by selecting or defining arbitrary regions or respective volumes of interest by using an Image Annotation Tool. Thus, clinical experts can indicate lymphatic occurrences by marking them on the image and subsequently labelling the body region with the corresponding RadLex concept. The output of the annotation procedure is used as input for the automated staging application, that is, the patient identifier and the patient's list of lymphatic occurrences are processed for the automatic generation of OWL-DL based patient representations.

In the context of automatic staging of lymphoma patients, the Ann-Arbor Staging System specifies the scope as well as the basic constraints for developing competency questions. Each of the staging classes matches with one high-level competency question and is represented as a complex and defined OWL DL class. This provides a basis for computing the answers, i.e. the patient classification. By representing patients as OWL classes with the corresponding axioms and characteristics, they can be classified according to their staging grade.

To determine the required concepts and axioms of the ontological model, the decision criteria of the Ann-Arbor Staging System need to be considered.

The staging can be seen as relying on three main different kinds of information, i.e. the number, the type and the relative position (in relation to the diaphragm) of lymphatic occurrences. In addition to this, the classification application is based on different knowledge resources, such as semantic image annotations, medical background knowledge and clinical guidelines. The relevant knowledge resources need to be preprocessed and customized for integration within the staging scenario. Thus, the requirements of the ontological model can be summarized as follows:

- To ensure the re-usability and interoperability of the patient data, integration of third party medical ontologies is required.
- To capture the above mentioned rationale of the Ann-Arbor Staging System, the ontological model needs to provide a basis for: inferring the number of lymphatic occurrences; identifying the relative location of the lymphatic occurrences—above, below or on both sides of the diaphragm—and for distinguishing the different types of lymphatic occurrences.
- The patient data needs to be represented accordingly. The above mentioned requirements are addressed in the following steps.

Scalable reasoning requires the modularization of large ontologies. These modules need to cover all concepts and relationships for describing the particular scenario—in our case, all concepts describing lymph node occurrences or extra lymphatic involvements. Thus, a RadLex fragment is semi-automatically generated in OWL DL format in accordance with the following steps:

As a scalable RadLex fragment covering all lymph node occurrences is required, all 'lymph node' concepts are selected automatically by using text-mining methods. 'Lymph node' concepts are those which contain the string 'lymph node' in the preferred name label, whilst 'node' concepts contain the string 'node' concept as super concept. The selecting step for a 'node' concept copes with the fact that RadLex Taxonomy encompasses lymph node occurrences— such as the concept 'rectural node'—that do not contain the full string 'lymph node', but are arranged as children of 'lymph node' concepts.

The resulting list encompasses a number of concepts representing relevant lymph node occurrences. A derived list of organs and regions representing possible extra nodal occurrences can be manually mapped onto the corresponding RadLex concepts. This list of RadLex concepts can be extended by the application relevant information and then used as an input file for the automatic generation of the OWL DL representation. This step can be realized via OWL API and paves the way for the inference of implicit conclusions relevant to the staging scenario.

The RadLex Taxonomy describes the parent-child relationship of concepts as a subclass relationship. In order to count concepts within the reasoning process, concepts need to be labelled as disjoint. As it is not possible to label a class and its subclass as disjoint, one can represent the semantics of the parent-child relationship as OWL DL axioms, such as RightLobarLymphnode—is_child_of.LobarLymphnode As the DL reasoner is only able to count concepts that are different, the selected concepts can be labelled as disjoint by adding the correlating axioms.

To indicate different types of lymphatic occurrences, i.e. for distinguishing lymph nodes and extra nodal occurrences, additional OWL DL axioms are added to the ontology model. For each RadLex concept, one of the following types of axiom is appended respectively.

AxiliaryLymphnode—is_type.lymphnode_type

Lung—is_type.extranodal_type

To distinguish and subsequently count the different types of lymphatic occurrences, the representation of the patient data is described accordingly.

In lymphoma staging, one differentiates between patients that only have lymphatic occurrences above, below, or on both sides of the diaphragm. Thus, the relative position of lymphatic occurrences constitutes an important decision criteria of the staging system and needs to be considered in the reasoning procedure. In other words, the underlying knowledge models needs to reflect the relative position of lymphatic occurrences in relation to the diaphragm. To achieve this, two alternative solutions can be seen. The information concerning the relative position of lymphatic occurrences can be either derived from the image segmentation algorithm or directly from the underlying ontological model. That is, this information either comes with the patient record information or with the integrated knowledge model of spatial position of lymphatic occurrences by segmentation algorithms. As RadLex does not explicitly capture the information about the relative position between lymphatic regions or organs and the diaphragm, the list of selected lymph node occurrences is enhanced accordingly before it is transformed to the OWL DL syntax. More precisely, each lymphatic region can be extended by an axiom, such as AxiliaryLymphnode—hasN_Location.aboveDiagram AbdominalLymphnode—hasN_Location.belowDiaphragm indicating that the region is respectively above or below the diaphragm. The classification of lymphatic regions—and or patients with lymphatic occurrence—above, below or on both sides of the diaphragm can be modelled as a value partition.

The patient's semantic medical image annotation can be used for generating the corresponding OWL DL presentation. The patient data can either be represented as concepts or instance data.

For both types of data, a correlated method for the automatic generation of the OWL DL code can be used.

In order to represent patients as concepts, they can be modelled as a subconcept of the concept 'Patient', which each lymph node occurrence being described by an axiom which indicates the existence of the lymph node. In addition, a closure axiom on the property 'hasLymphNodeOccurrence' is included, indicating that the property can only be filled by the set of all listed lymph node occurrences. A similar code is generated for all extra nodal occurrences. Two different properties can also be introduced—'hasLymphnodeOccurrence' and 'hasExtranodalOccurrence'—to enable the inference of the precise number of lymph nodes as well as of extra nodal occurrences.

To represent patients as instances, they can be modelled as instances of the concept 'Patient'. Each lymph node occurrence and extra nodal occurrence is captured as an object property assertion; lymph node occurrences with the property 'hasLymphnodeOccurrence', and extra nodal occurrence with the property 'hasExtranodalOccurrence'.

In order to answer given questions, one can break down complex competency questions that represent the made ontological commitment into simpler questions. These relate to the mentioned decision criteria of the Ann-Arbor Staging System and represent events that can be accessed independently. To access the number, relative position, and type of lymphatic occurrences, the following queries —that is, defined OWL classes —can be specified:

The OWL defined classes N1 and N2 subsume all patients with at least one or two involved lymph node regions.

The OWL defined classes E1 and E2 subsume all patients with at least one or two involved extra lymphatic organs or site involvements.

The OWL defined classes N_AllAboveD and N_allBelowD subsume all patients with the location of the lymph node regions either only above or below the diaphragm. To access patients with occurrences of lymph nodes on both sides of the diaphragm, the occurrences should not all be located above, or below, the diaphragm. This can be formulated by the complex class —N_AllAboveD —N_AllBelowD.

The location of extra nodal occurrences is identified in an analogous manner, i.e. by establish in the defined classes E_AllAboveD and E_AllBelowD, as well as the corresponding complex axiom for accessing patients with extra nodal occurrences on both sides of the diaphragm.

The final application queries are the Ann-Arbor Staging classes which are again represented as defined OWL DL classes. Each staging class captures the semantics as previously mentioned. Their formal representation makes use of the above introduced auxiliary classes the Ann-Arbor Staging Transformation. Stage-I is the union of the sets N1 and E1. The class N1 infers all patients with the involvement of at least one lymph node region and E1 all patients with the involvement of at least one extra lymphatic organ or site. Stage-II-mixed with Stage-II-N gathering all patients with more than two lymph node region that are all on one side of the diaphragm and Stage-II-mixed patients with one involved lymph node region and one involved extra lymphatic organ or site on the same side of the diaphragm. Patients of Stage-III are contained in Stage-III-N or in Stage-III-mixed. Stage-III-N identifies all patients that have at least two involved lymph node regions spread across both sides of the diaphragm and Stage-III-mixed all patients with one involved lymph node region and one involved extra lymphatic organ or site on both sides of the diaphragm. Stage-IV subsumes all patients that have two or more extra lymphatic organs or sites on both sides of the diaphragm.

What is claimed is:

1. A method for providing instance information data of an instance comprising:
generating a semantic representation of said instance on the basis of at least one instance data source by transforming annotated images taken of the instance by means of at least one image detection device into the semantic representation of the instance;
classifying one or more attributes of the instance at least in part on the basis of image coordinates;
generating a semantic representation of a domain on the basis of at least one structured domain data source, including:
accessing a domain ontology;
determining a context of the semantic representation of said instance; and
generating a fragment of the accessed domain ontology, including applying an automated filtering or mining process to the accessed domain ontology to exclude portions of the domain ontology unrelated to the determined context of the semantic representation of said instance;
performing an integration of the semantic representation of the instance and the semantic representation of the domain to provide an integrated semantic representation, the integrated semantic representation comprising a knowledge integration model, wherein the knowledge integration model defines an ontological structure of the semantic representation of the domain and the semantic representation of the instance;
deriving automatically instance information data from the provided integrated semantic representation; and
providing the automatically derived instance information data as a medical decision support or an instance process control.

2. The method according to claim 1, wherein said semantic representation of said instance comprises an instance ontology.

3. The method according to claim 1, wherein said instance is an object formed by a person or by a component.

4. The method according to claim 1, further comprising:
the semantic representation of the instance includes an instance ontology; and
the semantic representation of the domain includes a domain ontology;
wherein said instance ontology and said domain ontology are stored as web ontology language files.

5. The method according to claim 1, wherein said semantic representation of said domain is provided by extracting said semantic representation of said domain from a semantic representation of a top-level domain.

6. The method according to claim 5, wherein said semantic representation of said top-level domain is formed by a semantic representation of the anatomy domain or the radiology domain.

7. The method according to claim 1, wherein the integrated semantic representation is adapted to perform at least one of:
a semantic annotation of said instance,
a decision support for classification of said instance,
an instance search or
an instance process control.

8. A system for providing instance information data of an instance comprising:
at least one database storing a semantic representation of said instance and a semantic representation of a domain; and
a processing unit programmed to:
transform annotated images taken of the instance by means of at least one image detection device into a semantic representation of the instance;
classify one or more attributes of the instance at least in part on the basis of image coordinates;
generate a semantic representation of a domain by a process including:

accessing a domain ontology;
determining a context of the semantic representation of said instance; and
generating a fragment of the accessed domain ontology, including applying an automated filtering or mining process to the accessed domain ontology to exclude portions of the domain ontology unrelated to the determined context of the semantic representation of said instance;
at least one database storing the semantic representation of said instance and the semantic representation of a domain; and
wherein the processing unit is further programmed to:
perform an integration of the semantic representation of the instance and the semantic representation of the domain to provide an integrated semantic representation, the integrated semantic representation comprising a knowledge integration model, wherein the knowledge integration model defines an ontological structure of the semantic representation of the domain and the semantic representation of the instance;
automatically deriving instance information data from the integrated semantic representation; and
providing the automatically derived instance information data as a medical decision support or an instance process control.

9. The system according to claim 8, wherein said semantic representation of said instance is an instance ontology stored in a first database and said semantic representation of said domain is stored in a second database.

10. The system according to claim 9, wherein said instance ontology is stored as a web ontology language file in said first database and
said domain ontology is stored as a web ontology language file in said second database.

11. The system according to claim 8, wherein said processing unit is adapted to execute a reasoning engine which derives automatically the instance information data from the integrated semantic representation stored in said memory.

12. The system according to claim 8, wherein said semantic representation of said instance is generated by a transformation unit which transforms annotated images of said instance into said semantic representation of said instance.

13. The system according to claim 12, wherein said annotated images are provided by an annotation unit for annotating instance images taken of an instance.

14. The system according to claim 13, wherein said instance images are generated by means of at least one image detection device selected from the group consisting of:
a computer tomograph,
a magnet resonance imaging device,
an ultrasound detection device and
a positron emission tomograph.

15. The system according to claim 8, wherein said semantic representation of a domain comprises at least one of:
an Ann-Arbor Staging document providing a classification of lymphomas patients in terms of disease progression,
a foundation model of anatomy ontology and
a radiology lexicon ontology.

* * * * *